(12) United States Patent  (10) Patent No.: US 8,083,098 B1
Schaffer  (45) Date of Patent: Dec. 27, 2011

(54) STORAGE AND DISPENSING SYSTEM FOR NEEDLE-SHIELDS

(76) Inventor: Michael Schaffer, Coral Springs, FL (US)

( * ) Notice: Subject to any disclaimer, the term of this patent is extended or adjusted under 35 U.S.C. 154(b) by 924 days.

(21) Appl. No.: 12/032,242

(22) Filed: Feb. 15, 2008

Related U.S. Application Data

(60) Provisional application No. 60/902,733, filed on Feb. 22, 2007.

(51) Int. Cl.
*B65H 1/08* (2006.01)
(52) U.S. Cl. .......... 221/279; 221/65; 221/255; 221/226
(58) Field of Classification Search ............... 221/23, 221/65, 22, 25, 255–257, 279, 226
See application file for complete search history.

(56) References Cited

U.S. PATENT DOCUMENTS

| | | | | |
|---|---|---|---|---|
| 3,858,722 | A | * | 1/1975 | Haas .............................. 206/380 |
| 5,245,117 | A | * | 9/1993 | Withers et al. ................ 588/249 |
| 5,873,462 | A | * | 2/1999 | Nguyen et al. ................ 206/366 |
| 6,955,259 | B1 | | 10/2005 | Jesse |
| 7,134,550 | B2 | | 11/2006 | Groth |
| 7,201,736 | B2 | | 4/2007 | Hauri |
| 7,211,069 | B2 | | 5/2007 | Lehmann |
| 7,240,806 | B2 | | 7/2007 | Choi |
| 7,556,149 | B2 | * | 7/2009 | Erickson et al. .............. 206/366 |
| 7,815,046 | B2 | * | 10/2010 | Sansoucy et al. ............. 206/366 |
| 2003/0181871 | A1 | | 9/2003 | Wilkinson et al. |

* cited by examiner

*Primary Examiner* — Michael K Collins

(57) ABSTRACT

Devices, systems and methods of supplying needle covers to be used to cover or shield the sharp and contaminated ends of used syringe-needles. The devices, systems and methods can include a delivery mechanism sized and configured to supply a plurality of needle-shielding members arranged to automatically advance into a preferred position as each individual needle-shielding member is engaged and subsequently removed from the delivery mechanism.

14 Claims, 14 Drawing Sheets

STORAGE AND DISPENSING SYSTEM FOR NEEDLE-SHIELDS

This application claims the benefit of U.S. Provisional Application No. 60/902,733 filed Feb. 22, 2007.

FIELD OF INVENTION

The present invention relates generally to supplying needle covers to be used to cover or shield the sharp and contaminated ends of used syringe-needles, and more specifically to devices, mechanisms, systems and methods of having a delivery mechanism sized and configured to supply a plurality of needle-shielding members arranged to automatically advance into position as each individual needle-shielding member is engaged and subsequently removed from the delivery mechanism or system.

BACKGROUND AND PRIOR ART

Safe, convenient, cost-effective disposal of contaminated, used syringe needles remains elusive. Various shielding, cutting, melting and re-capping strategies have emerged and have been met with only limited success or acceptance. With the rise in the number and virulence of infectious diseases, the use of syringe needles by dentists, doctors, nurses, and other medical and emergency response personnel has made these individuals susceptible to injury and infection.

The inventor's prior invention discloses a base unit that contains a plurality of individual needle-shields that are sized and configured to stick onto a needle when said needle is inserted into the needle-shield. The individual needle-shields are arranged in a densely packed configuration. A preferred embodiment comprises a plurality of hexagon-shaped needle-shields packed in the configuration of a honeycomb. The distance between each needle-shield is very small so that a user of the device does not have to "aim" carefully at a single needle-shield element. A single disadvantage arises as the individual needle-shields are removed randomly. Empty pockets develop as the needle-shields are removed. At some point there are more empty pockets than there are filled pockets.

There remains a need for a needle-shield delivery mechanism that provides protection to healthcare workers from accidental pricks from used syringe needles. There is a further need for needle-shield system that provides a plurality of needle-shields in position for attachment to a needle at all times. An additional need exists for a user-friendly needle-shield mechanism that allows the healthcare practitioner to continue to perform their duties while availing themselves of the protections of this system. A still further need exists to provide a needle-shield delivery system that prevents exposure of the syringe needle once it has been covered with the shield.

Thus, the need exists for solutions to the above problems with the prior art.

SUMMARY OF THE INVENTION

A primary objective of the present invention is to provide devices, systems and methods for supplying needle covers to be used to cover or shield the sharp and contaminated ends of used syringe-needles.

Another feature of the invention is to provide a novel and improved devices, systems and methods for covering potentially dangerous and biohazardous implements comprising a new and improved delivery system which is easy to use and has a small footprint.

It is also a feature of the invention to provide a novel and improved devices, systems and methods for covering potentially dangerous and biohazardous implements, for example, hypodermic needles, by preventing contact between the potentially contaminated implement and the user.

It is another feature of the invention to provide a novel and improved devices, systems and methods for protecting individuals handling potentially dangerous and biohazardous implements, for example, syringe-needles by facilitating a person's ability to recognize when the delivery system has been entirely depleted.

In view of the foregoing, it is still another feature of the present invention, in embodiments, to provide a dispenser of needle-shields that automatically places a needle-shield in a position that allows a user to insert a needle-point into an easily accessible recess and withdraw a needle-shield when the needle is removed from the recess. In embodiments, as each needle-shield is removed, the next needle-shield in a spiral groove is automatically advanced into the "pick-up" position. There is, therefore, never an "empty pocket" until all needle-shields are used.

Further features, aspects, objects and advantages of this invention will be apparent from the following detailed description of the embodiments which are illustrated schematically in the accompanying drawings.

BRIEF DESCRIPTION OF THE FIGURES

FIG. 4 is an oblique top view of the present invention with the lid removed revealing the advancing groove and coil spring

DESCRIPTION OF THE PREFERRED EMBODIMENTS

Figure 1:
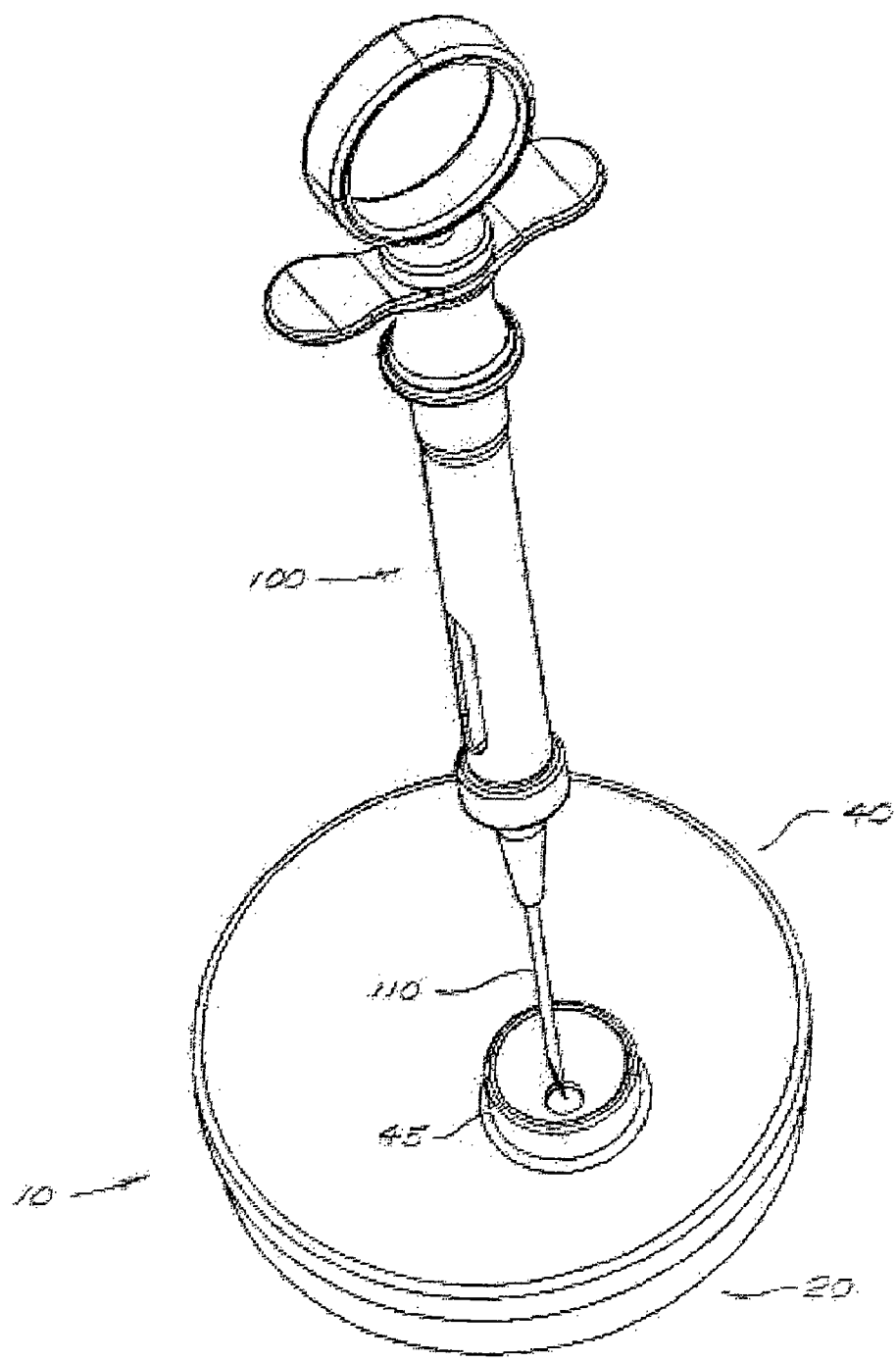
FIG. 1 is an oblique top view of the present invention and a syringe with a needle attached
Figure 2:
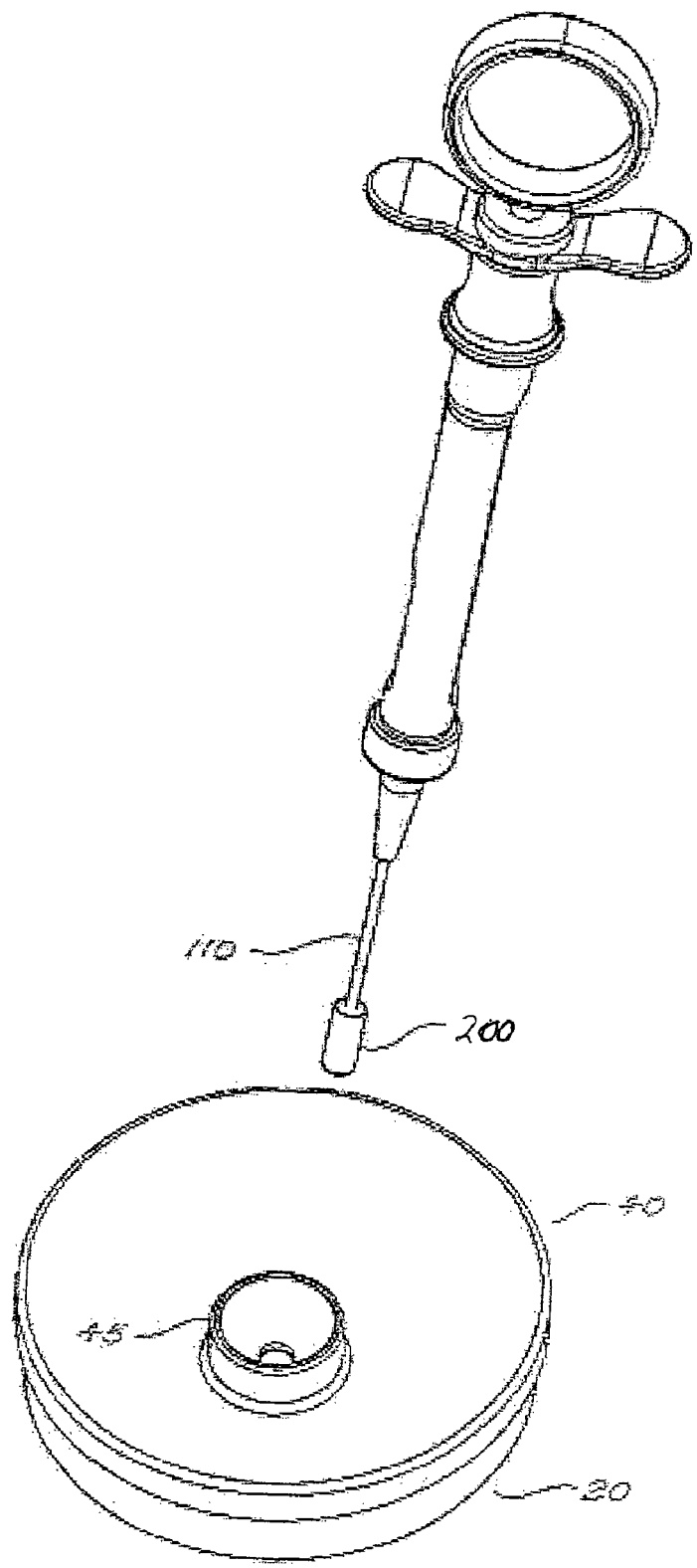
FIG. 2 is an oblique top view of the dispenser system of the present invention with a needle-shield attached to a syringe needle
Figure 3:
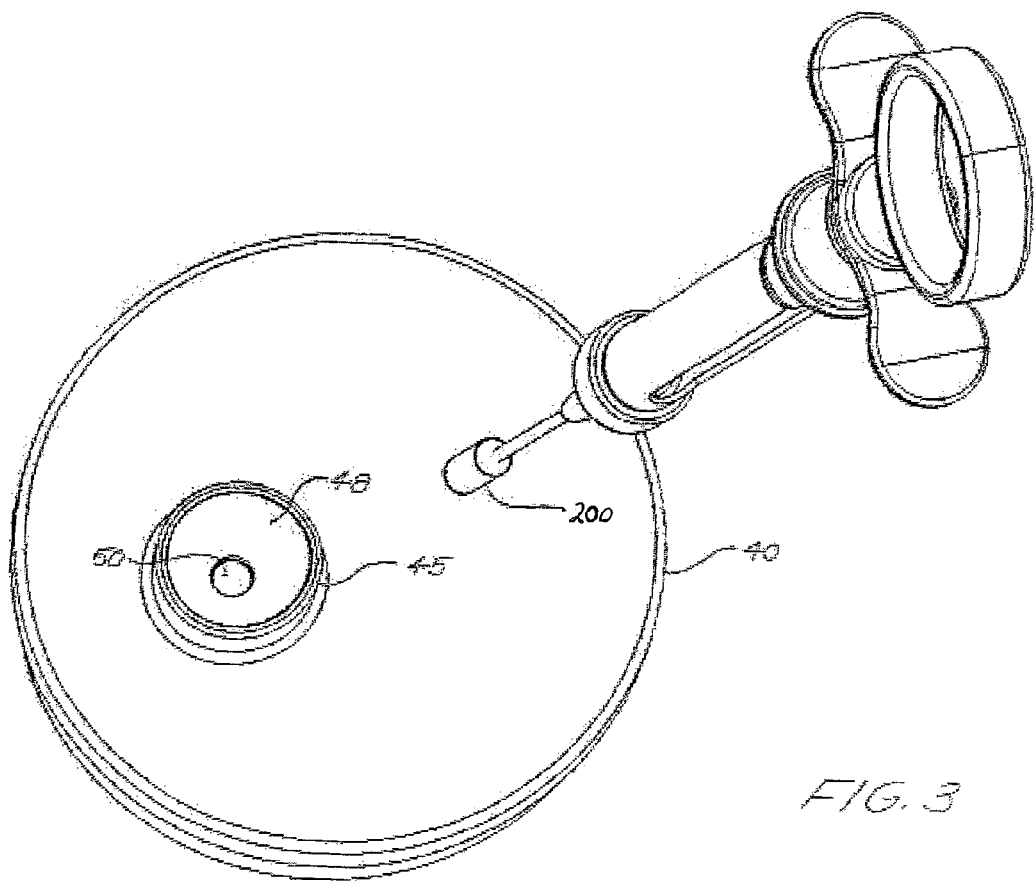
FIG. 3 is a users-eye-view of the dispenser system of the present invention with a needle-shield attached to a syringe needle
Figure 7:
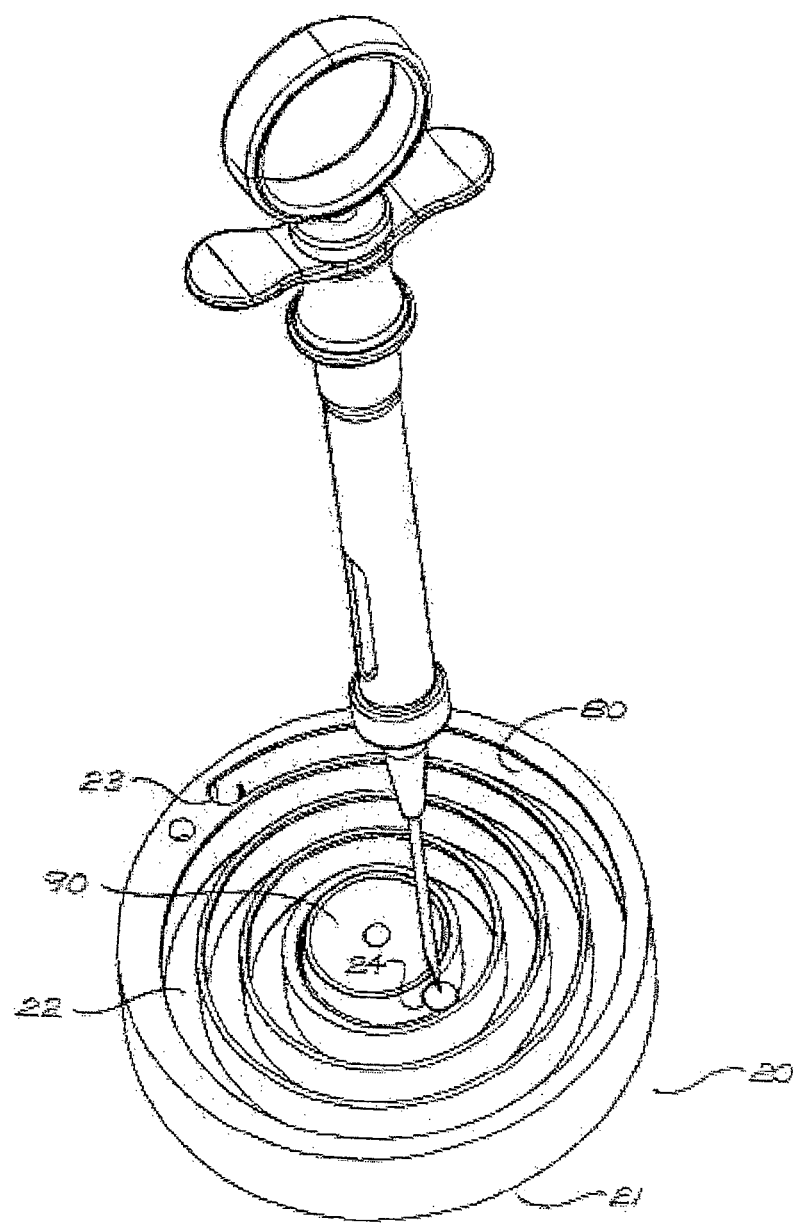
FIG. 7 is a top view

Before explaining the disclosed embodiments of the present invention in detail it is to be understood that the invention is not limited in its applications to the details of the particular arrangements shown since the invention is capable of other embodiments. Also, the terminology used herein is for the purpose of description and not of limitation.

In embodiments, the present invention provides a needle-shield storage and delivery devices, systems and methods comprising: a storage base having a delivery groove; a spring within said delivery groove; a plurality of needle-shields stored within said groove and held in sequential compression by said spring; and a base-cap sized and configured to hold said spring and plurality of needle-shields within said groove, the cap having an opening for releasing said needle-shields individually therefrom.

With reference to the drawings FIGS. 1, 2, 3 and 4 a dispensing mechanism 10 can comprise, in embodiments, a container base 20, a lid 40, a spring 80 and a plurality of individual needle-shields 200. A syringe 100 needle 110 can be inserted into a needle-shield 200 that is automatically advanced into position 50 by the continuous load of a coil spring 80 within a spiral pathway 22. The needle-shield 200 is withdrawn from position 50 when the needle 110 is removed from the dispensing mechanism 10 and remains attached to the needle 110. At this point the needle 110 can be safely re-capped or disposed of in an approved container. The individual needle-shields 200 can be comprised of, for example, a metal, celluloid, rayon, phenonlic, and polystyrene, and the like. The needle-shields 200 can also comprise, for example, a polyvinyl chloride, polyethylene, polymethyl and methacrylate.

In other embodiments, the needle-shields 200 can further comprise acrylics, silicones, polyurethanes, elastomers and engineering plastics. In embodiments, the individual needle-shields 200 can form, for example, the shape of a tube, cone, or sphere that is closed at one end and filled with, for example, an adhesive, glue, elastomer, foam or mechanical trap.

Figure 5:
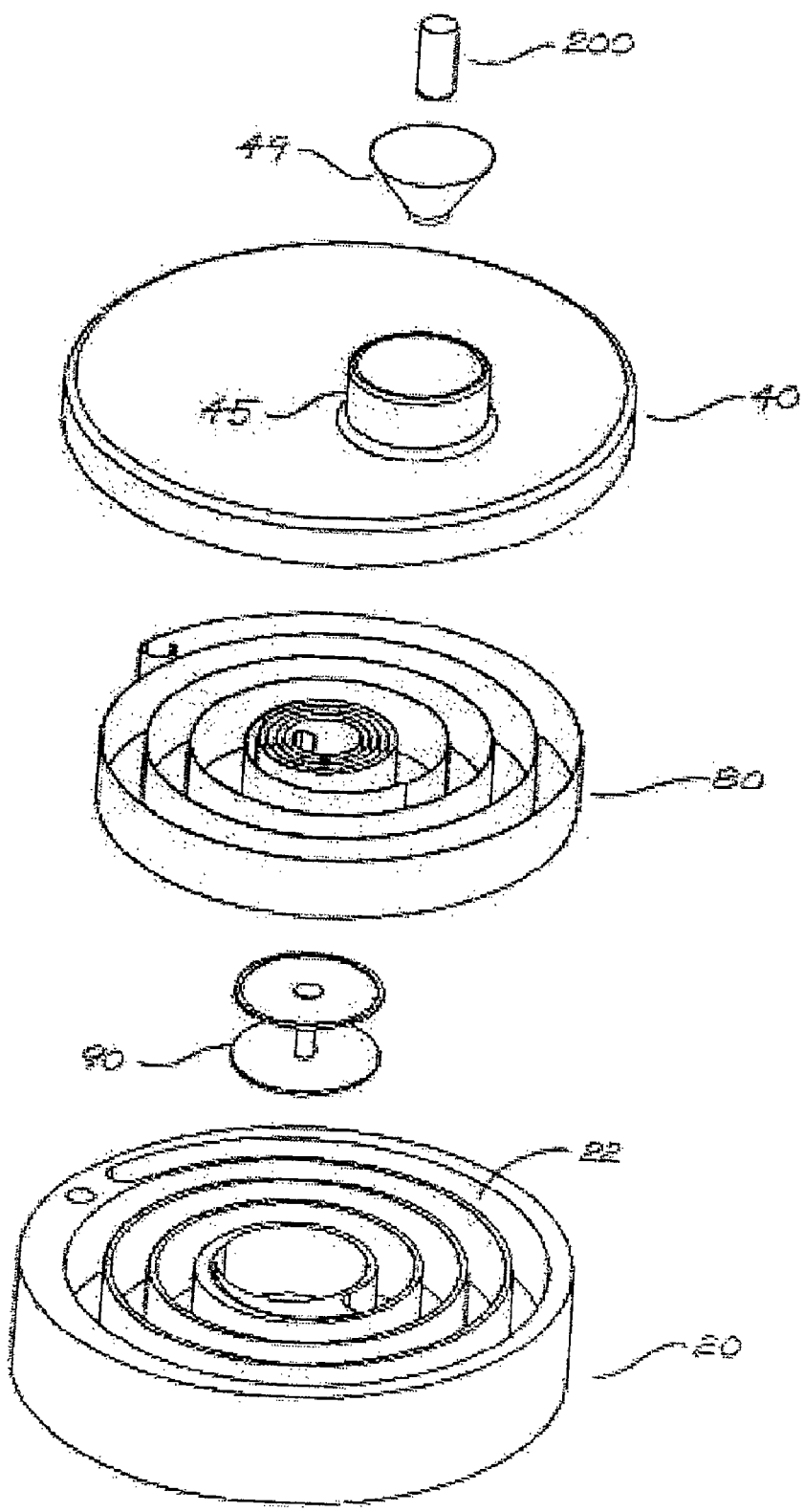
FIG. 5 is an oblique, exploded view revealing the individual components
Figure 6:
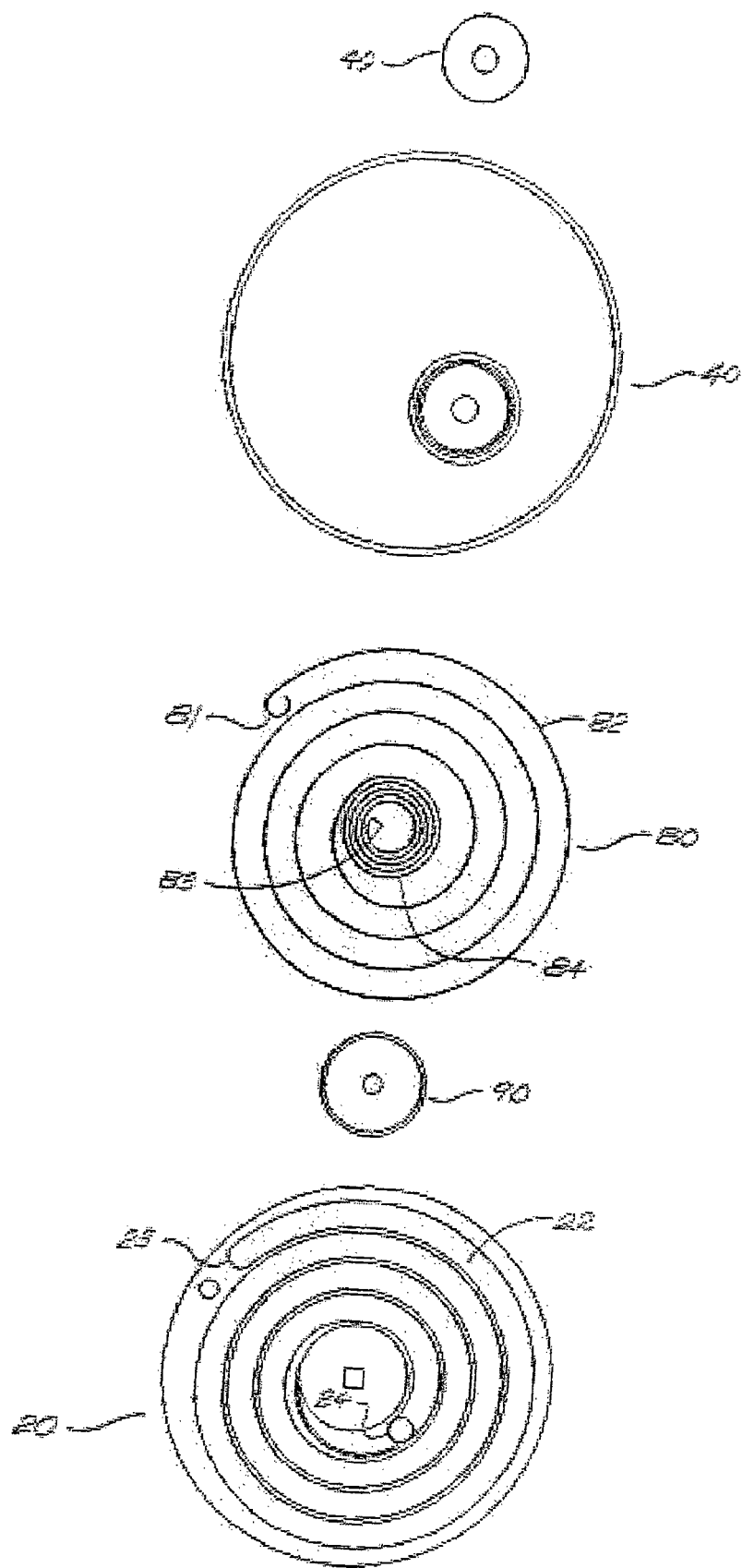
FIG. 6 is a top view of an embodiment of the invention with the individual components exploded to the side
Figure 7:
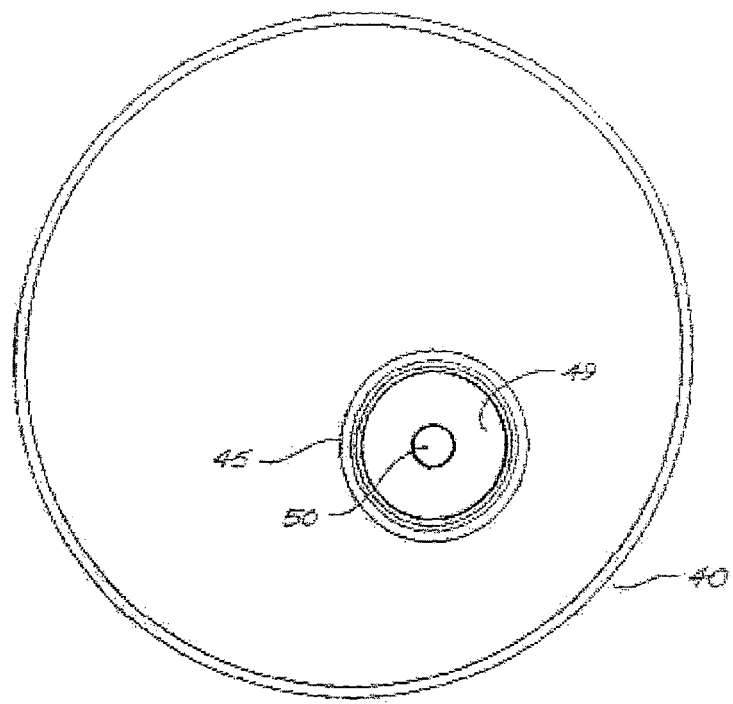

Referring now to FIGS. 4, 5 and 6 embodiments of the invention can comprise a base 20 that is sized and configured to contain a plurality of individual needle-shields 200, a coil spring 80, a winding-wheel 90 and a lid 40. The base 20 is supplied with a spiral slot or groove 22 that originates at the outer edge 21 of the base 20 and extends continuously inward to the center of the base 20 where it terminates at a point 24 adjacent to a central cavity or central bore 25. In embodiments, the termination point 24 is aligned with a graduated lead-in 45 associated with a lid 40 that fits onto the base 20 in alignment with the graduated lead-in 45. The graduated lead-in 45 can, in embodiments, form the shape of a circle, sphere, or cone. A portion 27 of the spiral groove 22 extends beyond the termination point 24 and is sized and configured to allow movement of the coil spring 80 as it winds upon the winding-wheel 90. The individual needle-shields 200 are held at the central termination point 24 by the constant force of the coil spring 80. In embodiments, the coil spring 80 can be comprised of, for example, aluminum, tin, silver, gold, copper, brass, bronze, carbon steel, chrome, titanium, and the like.

Figure 8:
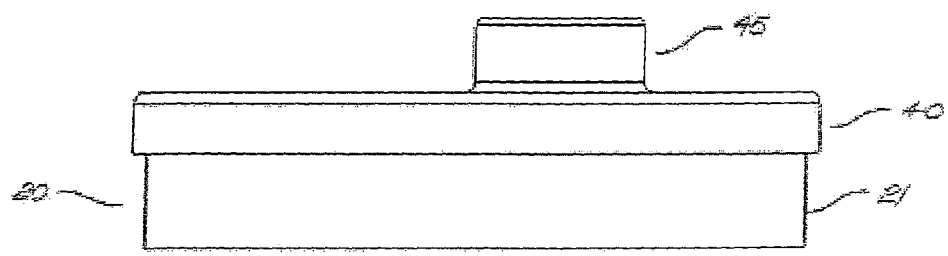
FIG. 8 is a side view
Figure 9:
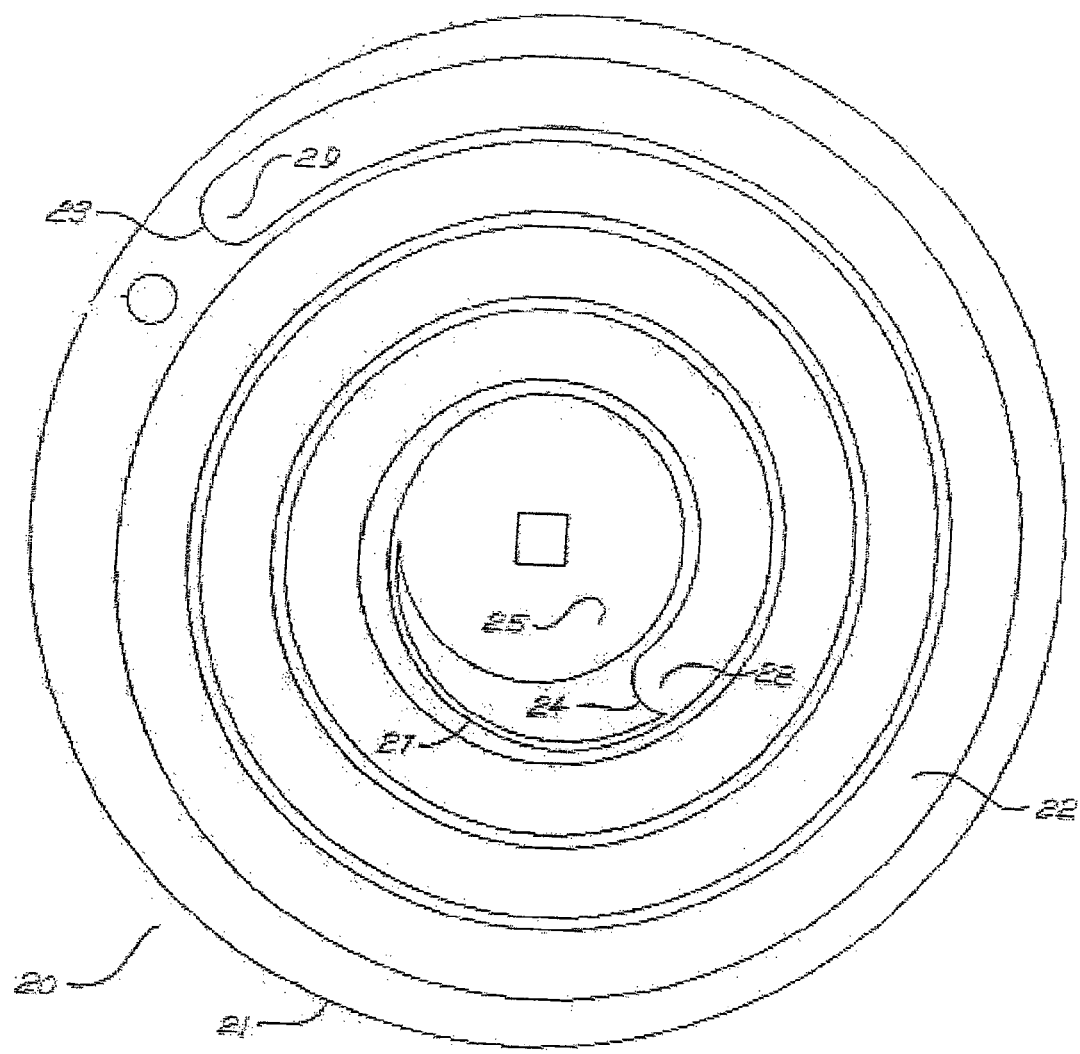
FIG. 9 is a detailed, enlarged top view of the base portion of the present invention with the lid removed
Figure 10:
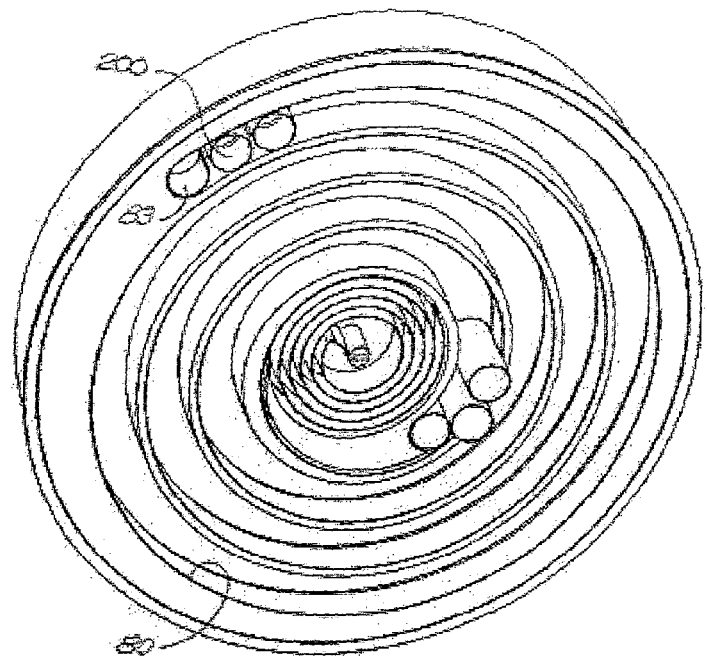
FIG. 10 is a perspective, top section-view of the base
Figure 11:
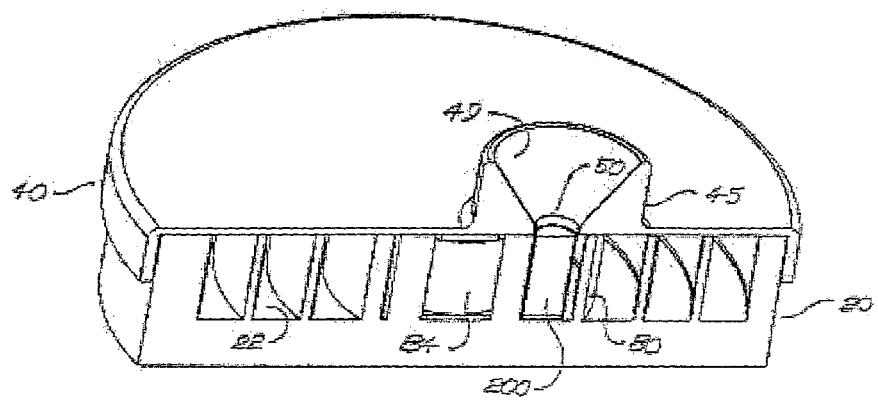
FIG. 11 is perspective, side section-view of the base
Figure 12:
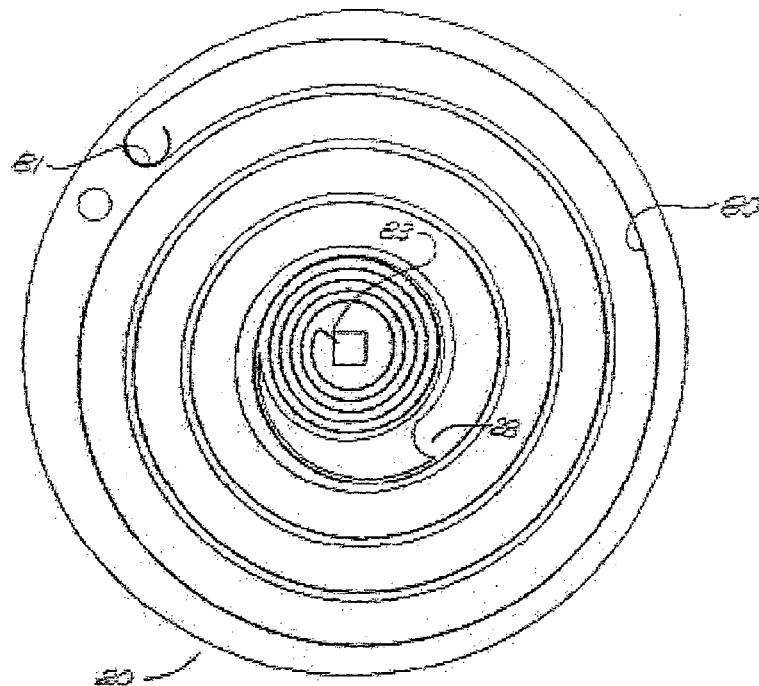
FIG. 12 illustrates the base from a top-view showing the placement of a coil spring
Figure 13:
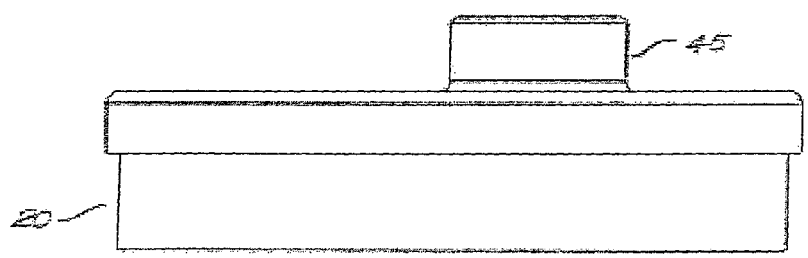
FIG. 13 is a side view
Figure 14:
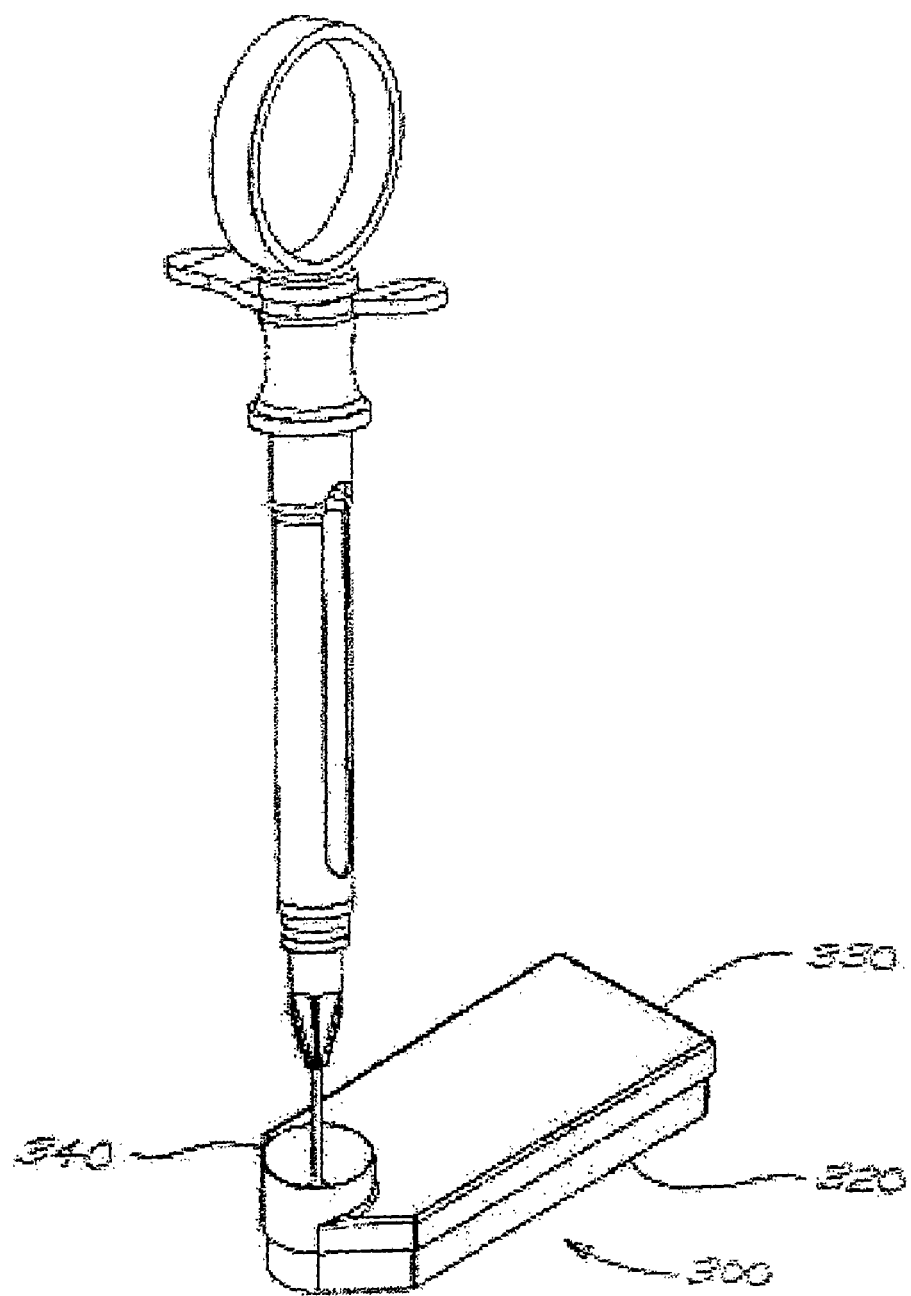
FIG. 14 is a perspective view of an alternate embodiment in use
Figure 15:
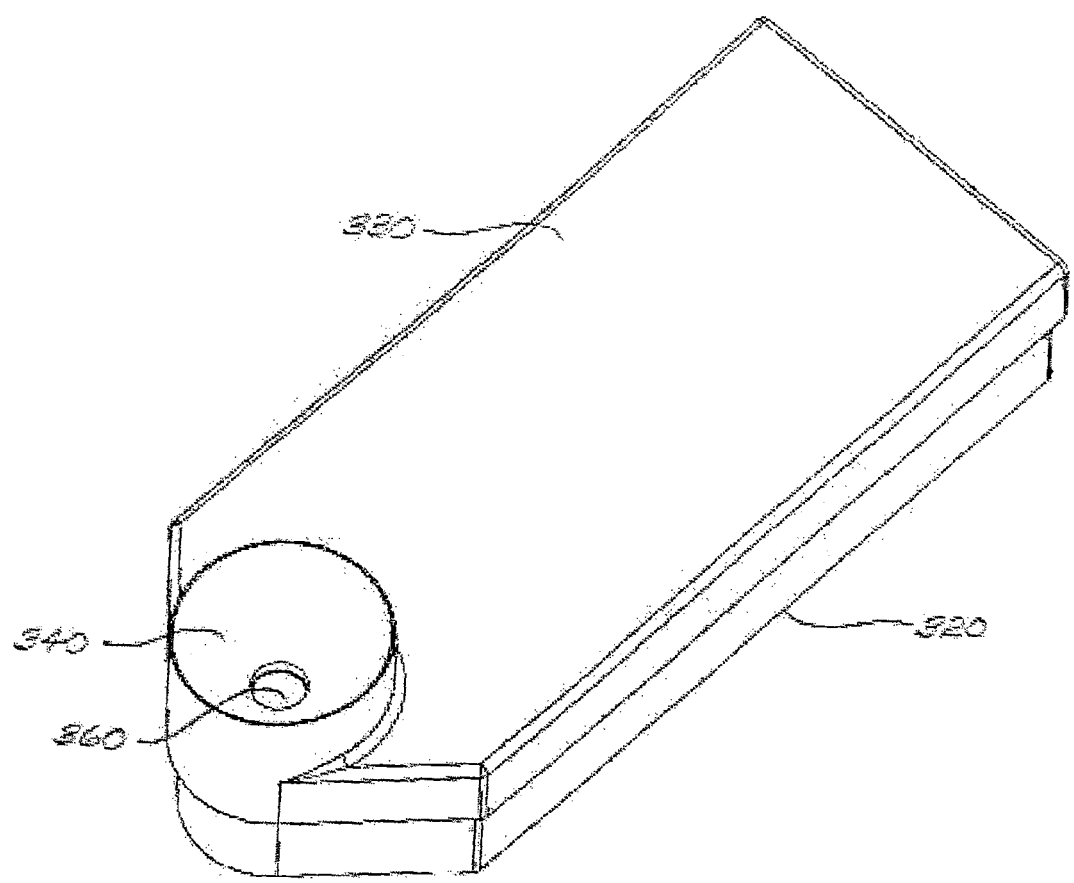
FIG. 15 is a perspective top view of an alternate embodiment comprising a linear delivery
Figure 16:
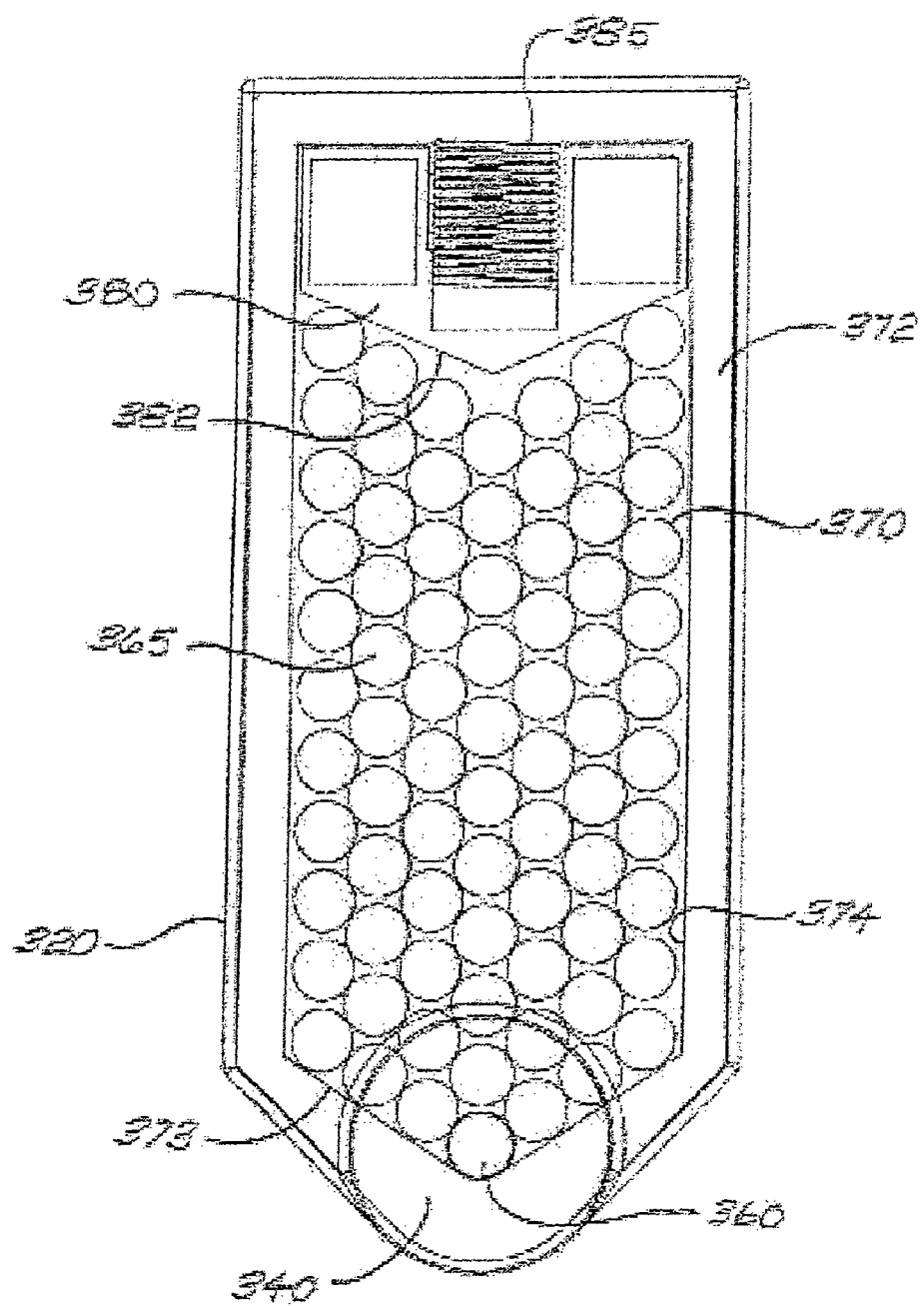
FIG. 16 is a top view of a linear arrangement with the cover removed
Figure 17:
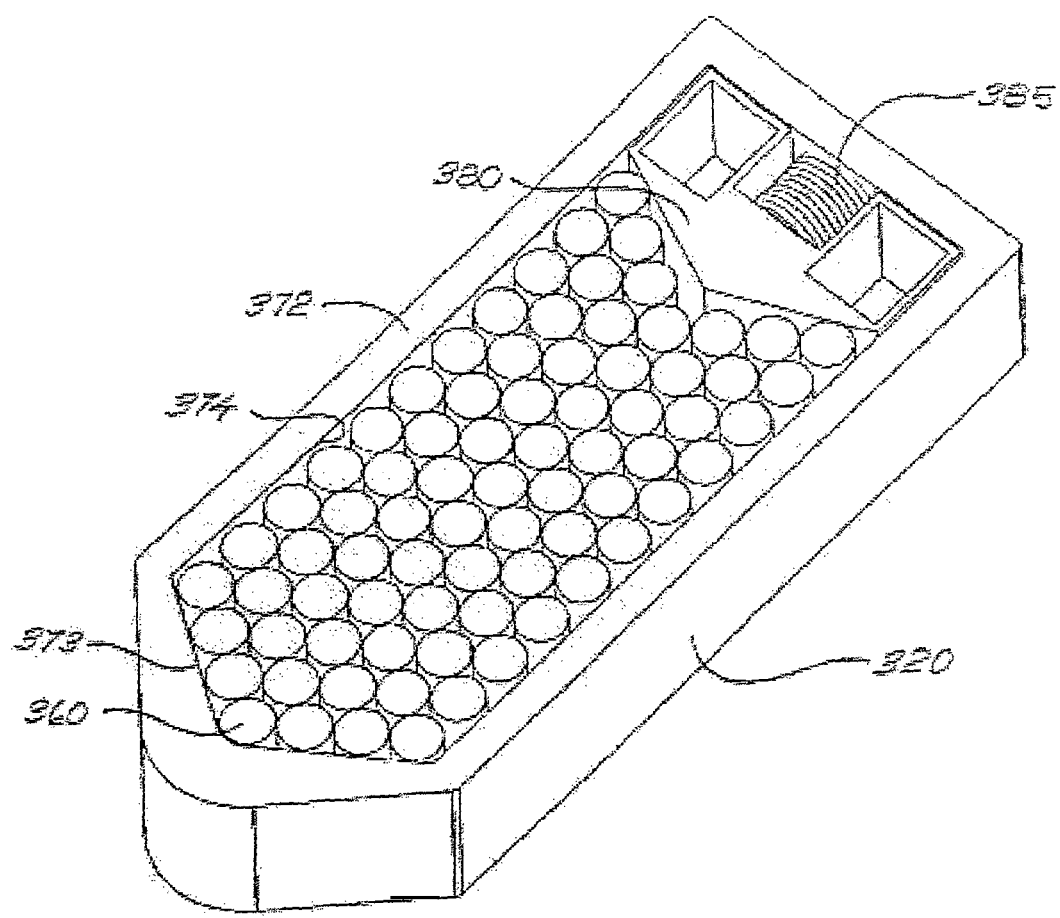
FIG. 17 is a perspective top view of a linear arrangement with the cover removed

With reference to FIGS. 8, 9 and 10 it can be seen that embodiments contemplate that the lead-in 45 associated with the lid or base-cap 40 can be somewhat off-center with respects to the overall shape of the base 20 and lid 40. The off-center configuration provides a maximum spring-length and total number of individual needle-shields 200 within the spiral groove 22. It can be seen that the general shape of the base 20 and lid 40 can vary. It could be round, oval, square and so on. The spiral grove 22 can be any of a number of pathways that represent a continuous groove from the edge 31 of the base 20 to the central bore 25. However, a preferred embodiment contemplates a substantially circular configuration since frictional forces are distributed somewhat equally along the spiral pathway 22. Embodiments also contemplate the use of round-tubular needle-shields 200 that are smoothly closed at the distal end. The round-tubular configuration allows the individual needle-shields 200 to rotate axially as they are advanced centrally under the influence of a constant force spring or a clock-spring 80. Allowance for axial rotation can minimize binding or friction in the event of an irregularity in the finish of an individual needle-shield 200 such as a burr or nick.

Referring to FIGS. 11, 12, 13 and 14 the base 20 of the present invention can be molded of a lubricious plastic, for example, polyethylene, polypropylene, nylon, polycarbonate, vinyl, ABS, PVC or the like. A hard-surfaced material can also be used, for example, cellulose or metal. The material selected provides low frictional resistance to the advancing needle-shield 200 so that the coil spring 80 can consist of a very thin material. A thin-metal coil or spring provides adequate continuous force to advance a plurality of needle-shields 200 into the termination point 24 for attachment to a needle 110. In embodiments, the coil spring 80 can have a thickness of from about 0.001 to about 0.01 inches, more particularly from about 0.001 to about 0.008 inches, and most particularly of from about 0.003 to about 0.005 inches. The coil spring 80 is first wound upon the winding-wheel 90 and inserted into the central bore 25 of the base 20. The winding-wheel 90 is configured to remain in place axially and not rotate within the central bore 25. The distal end 81 of the coil spring 80 is extended toward the outer end 23 the spiral groove 22. The spring coil 80 is then properly tensioned and has sufficient "potential energy" to advance the needle-shields 200 within the spiral groove 22.

The entire spiral groove 22 is filled with individual needle-shields 200. As the needle-shield 200 at the central termination point 24 is removed, the next needle-shield 200 in the spiral groove 22 is advanced into the central termination point 28, 50, until all of the needle-shields 200 are removed from the spiral groove 22 of the base 20. In embodiments, needle-shields are present in an amount of from about 1 to about 1000 needle-shields. In other embodiments, needle shields are present in an amount of from about 1 to about 500 needle-shields and in still further embodiments from about 1 to about 200 needle-shields. In embodiments, the dispensing mechanism 10 can be fully disposable or can be refilled with needle-shields 200.

The invention can be used to shield sharp needles 110 in preparation for re-capping or disposal. A user will aim the used needle 110 at the central graduated entry feature 45 or delivery channel 50 associated with the lid or base cap 40. the funnel, conical, or tubular shaped feature 45, 48 guides the sharp point of the needle 110 into the needle-shield 200 where it becomes attached to the contents of the needle-shield 200. In embodiments, the contents comprise materials chosen for tenacious adhesion to stainless steel needles 110. The attached needle 110 is withdrawn from the delivery channel 50 of the lid 40 and remains attached to the needle-shield 200. The force required to remove the needle-shield 200 from the delivery channel 50 is less that the force required to remove the needle-shield 200 from the needle 110 itself.

Referring to FIGS. 14-17 an alternate embodiment of the present invention is shown where the arrangement of needle-shield elements comprises an open channel 370 sized and configured to contain a plurality of needle-shield elements 365 in a linear, rectangular, modified rectangle, or square configuration and the like. The alternate embodiment can also comprise a straight channel or a plurality of converging channels that deliver a single needle-shield 365 into a preferred dispensing position 360. As illustrated, a base 320 can have an open channel 370 defined by a back wall 374, opposing side walls 372 and a front wall 373 that is configured to focus the advancement of needle-shields 365 to a central location 360. The needle-shields 365 are advanced by a driver 380 that is sized and configured to move linearly within the open channel 370 of the base 320. The motion of the advancing driver 380 is supplied by a compression spring 385 located between the rear-facing portion of the driver 380 and the back wall 374 of the base 320. The front portion 382 of the driver 380 is shaped so as to advance the needle-shields 365 in proportion to the shape of the front wall 373 of the base 320 so that the needle-shields 365 sequentially roll into the central position 360 beneath the entry cone 340 associated with the base-cover 330.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. A needle-shield storage and delivery mechanism comprising:
    a storage base having a continuous delivery groove;
    a lid for said storage base, wherein said storage base has a shape selected from the group consisting of a round shape, oval shape, a rectangular shape, and a square shape, and wherein said lid is in contact with said storage base while the delivery mechanism is in use;
    a constant force spring within said delivery groove, wherein said spring is made from the group consisting of aluminum, stainless steel, tin, silver, gold, copper, brass, bronze, carbon steel, chrome, and titanium;
    a plurality of not interconnected needle-shields stored within said groove and held in sequential compression by said spring, and further wherein said spring is adapted to slidably move said plurality of needle shields along said groove and wherein said needle-shields have a shape comprising tubular, spherical, elliptical, or conical, and further wherein said needle-shields are present in a range of from about 1 to about 500 needle-shields and wherein said needle-shields contact said spring while the delivery mechanism is in use; and
    a base-cap sized and configured to hold said spring and plurality of needle-shields within said groove, the cap having an opening for releasing said needle-shields individually there from, such that when a syringe needle is introduced through said opening and a needle-shield is thereby affixed to said syringe needle, upon removal from said opening the needle is capped for subsequent safe disposal and said spring unwinds to move said plurality of needle shields along said groove to position the next in line needle cap beneath said opening and still further wherein said cap is selected from the group consisting of steel, stainless steel alloys, aluminum, silver, brass, bronze, carbon steel, chrome, titanium, nickel-based alloys, polyethylene, polypropylene and silver-based alloys.

2. The storage and delivery mechanism of claim 1, wherein the groove further comprises:
    a spiral shaped delivery groove.

3. The storage and delivery mechanism according to claim 2, wherein the groove further comprises:
    a plurality of tubular shaped needle-shields.

4. The storage and delivery mechanism according to claim 2, wherein the groove further comprises:
    a plurality of conical shaped needle-shields.

5. The storage and delivery mechanism according to claim 3, wherein said groove is made from a flexible material selected from the group consisting of steel, stainless steel, aluminum, silver, gold, brass, bronze, carbon steel, chrome, titanium, a nickel-based alloy, a cobalt-based alloy, rubber, polyethylene, polypropylene, polystyrene and polybutylene.

6. The storage and delivery mechanism of claim 5, wherein the spring comprises:
    a coil shaped spring, and further wherein said spring has a thickness of from about 0.003 inches to about 0.005 inches.

7. The storage and delivery mechanism of claim 6, wherein said spring is comprised of stainless steel.

8. The mechanism of claim 7, wherein said base and base cap comprises:
    a dispenser for storing and dispensing needle-shields that are automatically advanced within said continuous channel for attachment to a sharp needle.

9. A needle-shield storage and delivery system for storing and dispensing needle-shields sequentially comprising:
    a storage and dispensing base having a continuous channel sized and configured to contain a plurality of individual not interconnected tubular needle-shields that are stored under a continuous spring load that is biased to present individual ones of said needle-shields sequentially to a single termination point;
    a lid for said storage base, wherein said storage base has a shape selected from the group consisting of a round shape, oval shape, a rectangular shape, and a square shape, and wherein said lid is in contact with said storage base while the needle-shield storage and delivery system is in use;
    a driver within said continuous channel, wherein said driver is made from the group consisting of aluminum, stainless steel, tin, silver, gold, copper, brass, bronze, carbon steel, chrome, and titanium, and further wherein said driver has a thickness of from about 0.003 inches to about 0.5 inches;
    a plurality of needle-shields stored within said continuous channel and held in sequential compression by said driver, wherein said needle-shields have a shape comprising tubular, spherical, elliptical, or conical, and further wherein said needle-shields are present in a range of from about 1 to about 500 needle-shields and wherein said needle-shields contact said driver while the delivery system is in use; and
    a base-cap sized and configured to hold said driver and plurality of needle-shields within said continuous channel, the cap having an opening for releasing said needle-shields individually there from, wherein when a syringe needle is introduced through said opening and a needle-shield is thereby affixed to said syringe needle, upon removal from said opening the needle is capped for subsequent safe disposal and still further wherein said cap is selected from the group consisting of steel, stainless steel alloys, aluminum, silver, brass, bronze, carbon steel, chrome, titanium, nickel-based alloys, polyethylene, polypropylene and silver-based alloys, and still further wherein said cap comprises an opening for the insertion of a syringe needle and the removal of said syringe needle with said needle-shield in place.

10. The storage and delivery system of claim 9, wherein the continuous channel further comprises:

a back wall, opposing side walls, and a front wall that is configured to focus the advancement of needle-shields to a central position.

11. The storage and delivery system of claim 10, wherein the continuous channel further comprises:
a plurality of tubular shaped needle-shields.

12. The storage and delivery system of claim 11, wherein said continuous channel comprises:
a driver that is sized and configured to move linearly within the continuous channel.

13. The storage and delivery system of claim 12, wherein said driver further comprises:
a coil shaped spring located between a rear-facing portion of the driver and a back wall of said base-cap.

14. The storage and delivery system of claim 13, wherein said continuous channel further comprises:
a plurality of converging channels.

* * * * *